United States Patent [19]

Richmond

[11] Patent Number: 4,642,091
[45] Date of Patent: Feb. 10, 1987

[54] STERILANT ADDITIVE HOLDER FOR CAPD SETS

[75] Inventor: Douglass S. Richmond, Mission Viejo, Calif.

[73] Assignee: Kendall McGaw Laboratories, Inc., Irvine, Calif.

[21] Appl. No.: 709,903

[22] Filed: Mar. 8, 1985

[51] Int. Cl.$^4$ ............................................. A61M 1/28
[52] U.S. Cl. .................................. 604/29; 604/283; 604/905; 128/DIG. 26
[58] Field of Search ................... 604/29, 80, 283, 411, 604/905, 256, 174, 175, 180; 128/DIG. 26, 6; 422/297, 293, 28, 292; 248/205 A

[56] References Cited

U.S. PATENT DOCUMENTS

| | | | |
|---|---|---|---|
| 2,421,103 | 2/1943 | Wadsworth | 285/61 |
| 4,209,013 | 6/1980 | Alexander et al. | |
| 4,354,490 | 10/1982 | Rogers | |
| 4,402,691 | 9/1983 | Rosenthal et al. | |
| 4,432,764 | 2/1984 | Lopez | 604/283 |
| 4,432,766 | 2/1984 | Bellotti et al. | |

Primary Examiner—Stephen C. Pellegrino
Assistant Examiner—John D. Ferros
Attorney, Agent, or Firm—John A. Kane

[57] ABSTRACT

A disposable "third hand" holder for CAPD exchange sets holds a set connector and a cap in an aseptic condition until ready for use. The holder is adhesively secured to a work surface. After the set connector has been removed from the holder and the exchange is under way, a sterilant tube can be connected to the holder in place of the set connector, and its contents can be squeezed out through a passage within the holder into the interior of the cap. When the patient's catheter is eventually capped, the sterilant in the cap maintains all interior surfaces of the catheter connector in an aseptic condition.

6 Claims, 6 Drawing Figures

STERILANT ADDITIVE HOLDER FOR CAPD SETS

FIELD OF THE INVENTION

This invention relates to aseptic holders for CAPD connectors, and more particularly to a holder in which sterilant can be efficiently added to a connector cap without removing the cap from the holder.

BACKGROUND OF THE INVENTION

Continuous ambulatory peritoneal dialysis (CAPD) is a commonly used therapeutic technique which has the advantage of allowing a patient to perform dialysis without recourse to a hospital or other clinical facility. Basically, a catheter is implanted in the patient, and apparatus is connected to this catheter for introducing dialysis fluid into the peritoneal cavity and withdrawing it therefrom after dialysis has taken place. The procedure involves the connection of the patient's catheter to, and its disconnection from, various fluid containers in the course of a fluid exchange.

Because the procedure is normally carried out by the patient himself in a septic environment, great caution must be exercised to prevent contamination of the dialysis fluid with bacteria capable of causing peritonitis. Indeed, statistical studies show that CAPD patients using some prior art exchange devices contract peritonitis on the average of once every four months whereas patients undergoing the very similar continuous cycling peritoneal dialysis therapy (CCPD), which is performed in a clinical environment, contract peritonitis only about once every two years on the average.

There consequently exists a need for a fluid exchange apparatus for CAPD in which there is a minimum chance of contamination of any fluid-contacting surfaces by the patient's hands, the furniture in the room, or airborne bacteria.

In a widely used prior art device, a fluid exchange involves the drainage of spent dialysis fluid into a used-fluid bag; the disconnection of a needle-shaped connector from the used-fluid bag; the insertion of the connector into a fresh-fluid bag; and the drainage of the fresh fluid into the patient's peritoneal cavity. During the switch from the used-fluid bag to the fresh-fluid bag, careless patients were frequently tempted to momentarily set the connector down on a septic work surface where it would become contaminated. Bacteria deposited on the tip of the connector would then be flushed into the peritoneal cavity during the infusion of the fresh dialysis fluid.

It was subsequently proposed to provide a system in which the used-fluid container and the fresh-fluid container were aseptically connected to a single, valved system prior to the exchange. The assembled aseptic system was then connected to the patient's catheter in a single motion, and remained so connected throughout the exchange. Following the exchange, the patient's catheter was capped with an aseptic cap. Connectors with recessed, shrouded conduits mated by a luer taper were used to minimize the chance of the patient's hands contacting elements of the fluid path.

In order to hold the system connector in an aseptic condition until it was ready to be connected to the patient's catheter, it was next proposed to provide a holder which could be adhesively secured to a work surface, and which held the system connector in an aseptic condition until ready for use. The holder also held a cap in contact with a sponge. During the fluid drainage or infusion (which takes some time), the cap could be lifted off the holder, the sponge could be saturated with a sterilant, and the cap could then be replaced onto the sponge so as to coat with sterilant at least some of the portions of the cap which would eventually be inserted into the patient's catheter connector.

Although the last-mentioned arrangement assured a substantial amount of sterility, there was still a chance of contamination of some interior portions of the cap which were not reached by the sterilant. It was therefore desirable to provide a holder in which sterilant could not only be added to the cap without removing the cap from the holder, but in which the sterilant would also coat virtually all of the interior surfaces of the cap.

SUMMARY OF THE INVENTION

The invention fills the above-stated need by providing a disposable holder which can be affixed to a work surface such as a table and which serves the dual purpose of maintaining the exchange set connector in a sterile condition until it is ready to be connected to the catheter connector, and of allowing the efficient introduction of sterilant into the cap without removing the cap from the holder.

The holder of this invention accomplishes this dual purpose by providing a body which is adhesively securable to a work surface, and a passage through that body connecting a fitting for the set connector to a fitting for the cap. The cap fitting is sufficiently resilient or loose so that if sterilant is introduced into the set connector fitting under slight pressure, it will travel through the passage and coat all the interior surfaces of the connector.

The fittings on the holder are preferably positioned at right angles to each other, for ease of manipulation, and with the cap fitting vertical to provide for uniform distribution of the sterilant.

DESCRIPTION OF THE PREFERRED EMBODIMENT

Figure 1:
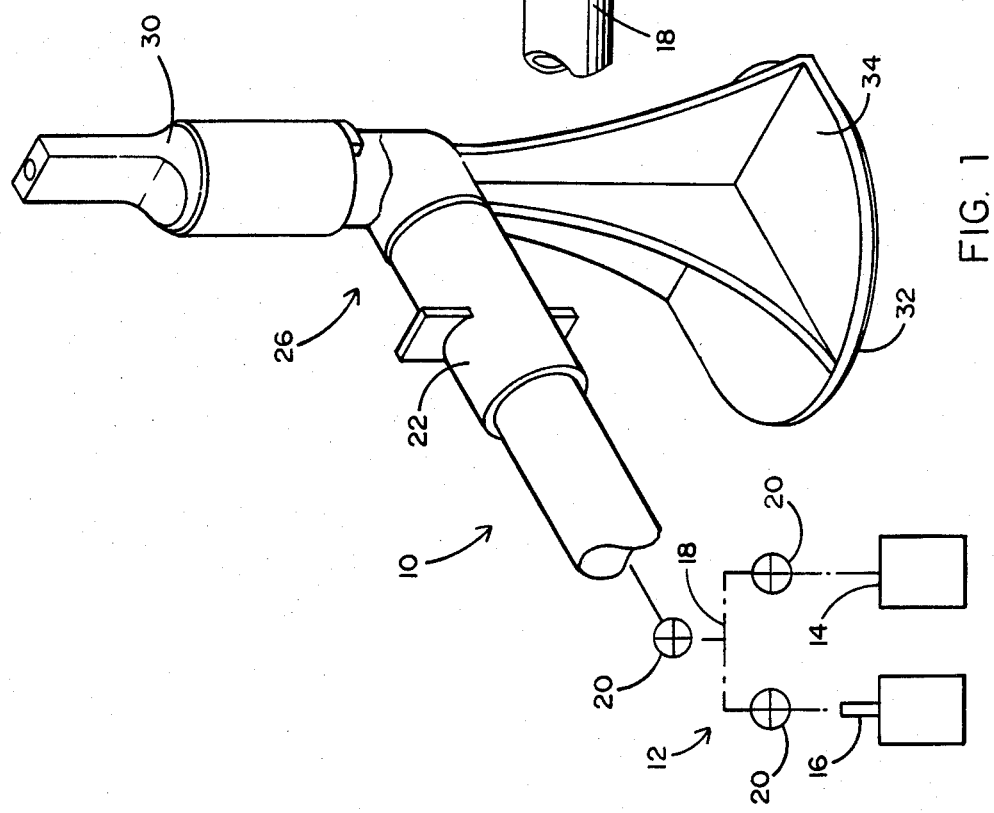
FIG. 1 is a perspective view, partly schematic, illustrating the device of the invention as supplied to the patient.
Figure 6:
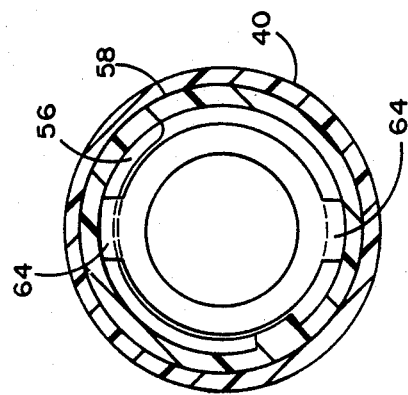
FIG. 6 is a horizontal section along line 6—6 of FIG. 5.
Figure 3:
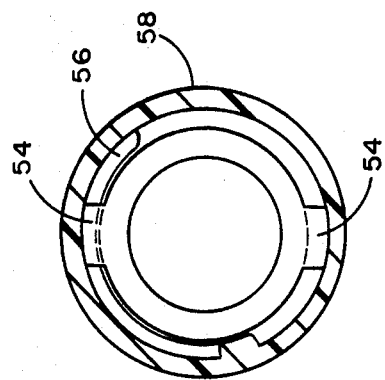
FIG. 3 is a horizontal section along line 3—3 of FIG. 2.
Figure 5:
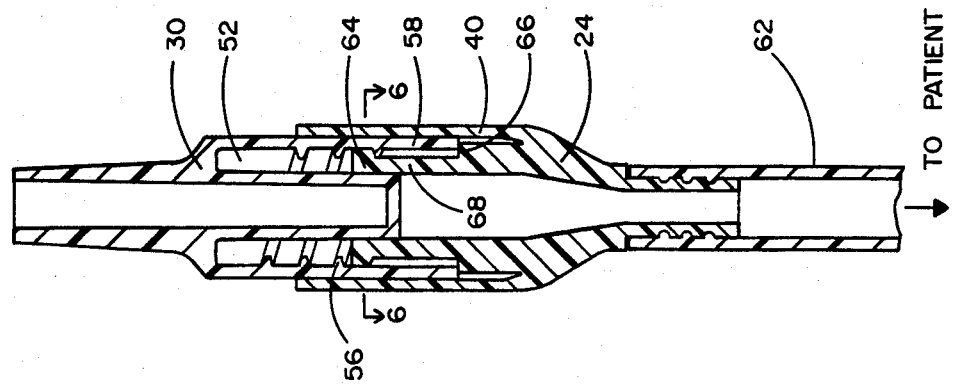
FIG. 5 is a vertical section of the capped connector to the patient's catheter.

FIG. 1 illustrates the device of this invention as it is furnished to the patient. An exchange set 10 packed in a sterile package (not shown) contains a sterile valved system 12 which includes a drainage bag 14, a connector 16 for the aseptic connection of the tubing 18 to a dialysis solution container, valves or clamps 20 to control the fluid flow through tubing 18, and a set connector 22 which will eventually be connected to the patient's catheter connector 24 of FIG. 5.

As packed in the sterile package, the set connector 22 is attached to a holder 26 which is the subject of this invention. The holder 26 has an interior passage 28 (FIG. 2) whose ends, in the packaged condition, are closed off, respectively, by the set connector 22 and the cap 30 which will eventually be used to cap the catheter connector 24 of FIG. 5 after the fluid exchange is completed.

Following its removal from the sterile package, the holder 26 is attached to a work surface 31 by an adhesive pad 32 attached to the base 34 of holder 26. The system 12 can then be set up and prepared for operation without exposing the interior of set connector 22 to handling or airborne contamination.

Figure 2:
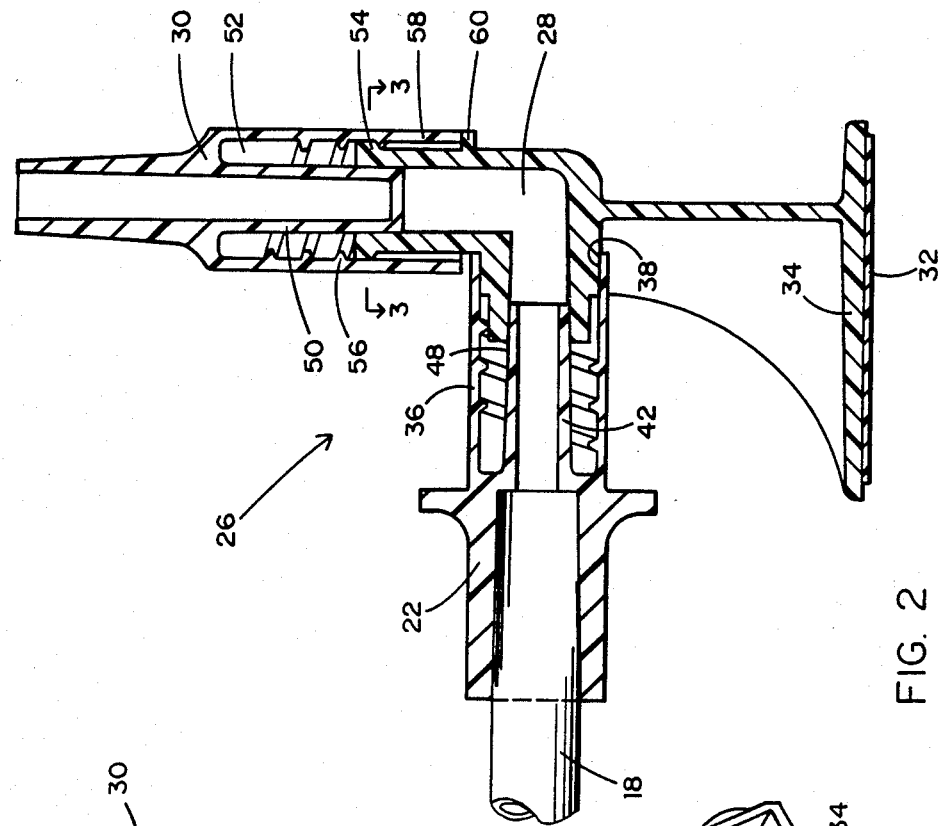
FIG. 2 is a vertical section of the device of this invention.

Referring now to FIG. 2, the outer end of the shroud 36 of set connector 22 is press-fitted onto the circular shoulder 38 of holder 26. When the exchange set is set up and ready to go, the existing cap 30 on the catheter connector 24 (FIG. 5) is removed and discarded. The set connector 22 is then pulled off the holder 26 and rapidly connected to the catheter connector 24 of FIG. 5. During this operation, the shroud 36 of the set connector 22 and the shroud 40 of catheter connector 24 protect the male luer 42 of set connector 22 and the female luer 68 (FIG. 5) of catheter connector 24 from handling contamination, and both luers are exposed to airborne contamination for only an insignificantly short period of time.

Figure 4:
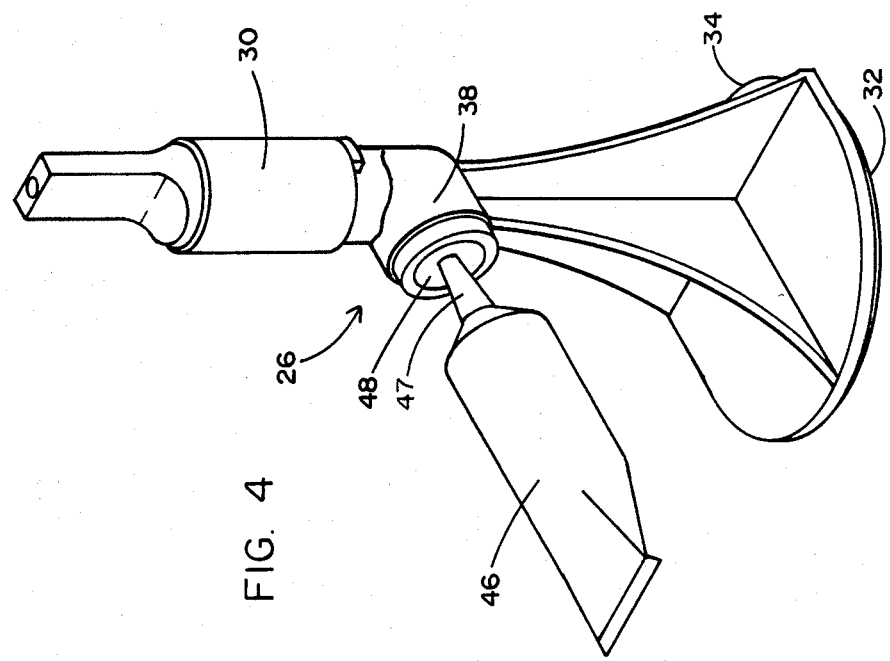
FIG. 4 is a perspective view of the device of this invention during insertion of the sterilant.

While the fluid exchange takes place, a flexible sterilant tube 46 (FIG. 4) with a male luer tip 47 is opened and inserted into the female luer 48 of holder 26. When the tube 46 is squeezed, sterilant is pushed through the passage 28 (FIG. 2), past the rather loose fit of male luer 50 in passage 28, into the cavity 52 of cap 30. From there, it flows around the ears 54 (onto which the cap 30 is screwed by screwthreads 56 until its shroud 58 abuts against the stop 60 of holder 26, thus limiting the insertion of luer 50 into passage 28), and down along the inside of shroud 58. The amount of sterilant in tube 46 is preferably such that, when tube 46 is squeezed, sterilant will coat all the interior surfaces of cap 30 but will not substantially flow out of cap 30.

In the preferred embodiment of the invention, the passage 28 (FIG. 2) is L-shaped, and the cap 30 rests on it in a vertical position. This is done so that the sterilant will distribute itself evenly around the interior of cap 30, rather than accumulate on one side. By contrast, the set connector 22 fits horizontally onto the holder 26 so that it may be conveniently pulled off without tending to pull the holder 26 up from the work surface 31.

When the exchange of dialysis fluid has been completed, the set connector 22 is disconnected from the catheter connector 24 (FIG. 5) which forms the outer end of the patient's implanted catheter 62. The entire exchange set, including the set connector 22, is then discarded. The cap 30 is now unscrewed from holder 26, inserted into the catheter connector 24, and tightened by screwing screwthreads 56 onto ears 64 until the cap shroud 58 abuts against the shoulder 66 of connector 24.

In the course of capping catheter connector 24, the sterilant-coated interior surfaces of cap 30 and the sterilant-filled cavity 52 deposit sterilant onto both the exterior and interior surfaces of the female luer 68 of catheter connector 24, as well as on the ears 64. As a result, any interior surfaces of the catheter connector 24 which might have been subjected to airborne contamination prior to capping are adequately sterilized.

Following capping, the holder 26 is detached from the work surface 31 and is discarded, together with the still attached sterilant tube 46.

I claim:

1. A sterilant-additive holder for CAPD exchange sets, comprising:
   (a) a body adhesively securable to a work surface, said body having a passage extending therethrough;
   (b) connector retaining means on said body for releasably retaining a CAPD set connector in aseptic communication with said passage; and
   (c) cap retaining means on said body for releasably retaining a CAPD catheter connector cap in aspetic communication with said passage;
   (d) said passage extending from said connector retaining means to said cap retaining means; and
   (e) said cap having a portion closing off said passage when said cap is retained on said holder, the fit between said portion and said passage being sufficiently loose to allow sterilant introduced into said passage under pressure to penetrate into the interior of said cap.

2. The holder of claim 1, further including limiting means for limiting the depth of insertion of said portion into said passage.

3. The holder of claim 1, in which said connector retaining means include a female luer fitting adapted to receive the male fitting of a sterilant tube in pressure-tight relationship.

4. A sterilant-additive holder for CAPD exchange sets, comprising:
   (a) a body adhesively securable to a work surface, said body having a passage extending therethrough;
   (b) connector retaining means on said body for releasably retaining a CAPD set connector in aseptic communication with said passage; and
   (c) cap retaining means on said body for releasably retaining a CAPD catheter connector cap in aseptic communication with said passage;
   (d) said passage extending from said connector retaining means to said cap retaining means; and
   (e) said connector retaining means receiving said connector in a sliding relationship, said cap retaining means including ear means cooperating with screwthreads inside said cap to secure said cap to said holder.

5. A sterilant-additive holder for CAPD exchange sets, comprising:
   (a) a body adhesively securable to a work surface, said body having a passage extending therethrough;
   (b) connector retaining means on said body for releasably retaining a CAPD set connector in aseptic communication with said passage;
   (c) cap retaining means on said body for releasably retaining a CAPD catheter connector cap in aseptic communication with said passage; and
   (d) an adhesive pad secured to the underside of said holder;
   (e) said passage extending from said connector retaining means to said cap retaining means.

6. A sterilant-additive holder for continuous ambulatory peritoneal dialysis (CAPD) exchange sets, comprising:
   (a) a body having a passage extending therethrough;

(b) adhesive means on said body for securing said body to a work surface;
(c) connector retaining means on said body;
(d) CAPD set connector means releasably retained on said retaining means to aseptic communication with said passage;
(e) cap retaining means on said body; and
(f) CAPD catheter connector cap means releasably retained is aseptic communication with said passage;
(g) said passage extending from said connector retaining means to said cap retaining means wherein said passage is generally L-shaped, said cap being retained in a generally vertical position and said connector being retained in a generally horizontal position.

* * * * *